United States Patent [19]
Lemelson

[11] Patent Number: 5,480,562
[45] Date of Patent: Jan. 2, 1996

[54] METHOD OF PURIFYING WATER CONTROLLED BY LASER SCANNING

[76] Inventor: Jerome H. Lemelson, Suite 286, Unit 802, 930 Tahoe Blvd., Incline Village, Nev. 89451-9436

[21] Appl. No.: 173,972

[22] Filed: Dec. 28, 1993

[51] Int. Cl.$^6$ .................................................... B01D 17/12
[52] U.S. Cl. .................... 210/745; 210/94; 210/96.1; 210/764; 348/552; 356/318; 356/436; 364/525; 436/55; 436/172; 436/164
[58] Field of Search ............................. 210/85, 94, 96.1, 210/143, 198.1, 745, 746, 748, 764; 422/62, 82.05, 82.08, 82.09; 436/39, 55, 164, 172; 364/497, 500, 525; 356/318, 436, 441; 348/552

[56] References Cited

U.S. PATENT DOCUMENTS

| | | | |
|---|---|---|---|
| 4,013,552 | 3/1977 | Kreuter | 210/748 |
| 4,766,550 | 8/1988 | Byers et al. | 422/62 |
| 5,030,419 | 7/1991 | Ellis et al. | 422/82.05 |
| 5,242,602 | 9/1993 | Richardson et al. | 364/500 |

FOREIGN PATENT DOCUMENTS

| | | | |
|---|---|---|---|
| 2355565 | 5/1975 | Germany | 436/164 |
| 4109118 | 9/1992 | Germany | 422/82.05 |
| 4326993 | 11/1992 | Japan | 210/96.1 |

OTHER PUBLICATIONS

"Remote determination of the concentration of impurities in water by the laser spectroscopy method with calibration by Raman scattering", D. N. Klyshko and V. V. Fudeer, Soviet Phys. Dekl. 23(1) January 1978 and printed in 1978 American Institute of Physics, pp. 55–57.

Primary Examiner—Joseph W. Drodge
Attorney, Agent, or Firm—J. Kevin Parker

[57] ABSTRACT

A system and method is disclosed for purifying water for drinking or bathing purposes employing an optical scanning device for detecting organisms in the water such as bacteria, algae, or viruses. The optical scanning device may be a video camera or may comprise a laser for irradiating the organisms and a photodetector for detecting radiation emanating from the organisms. A computer analyzes scanning signals generated by the scanning device and controls a device for neutralizing the organisms, such as a chemical injector or radiation source, in accordance with the scanning signals. The system may also be used to detect and neutralize disease producing organisms in a body fluid of a patient or in any fluid used for biological experimentation, testing, or production.

18 Claims, 3 Drawing Sheets

METHOD OF PURIFYING WATER CONTROLLED BY LASER SCANNING

BACKGROUND AND SUMMARY OF THE INVENTION

This invention relates to a system and method for purifying water, such as drinking water and pool water, by controllably killing or otherwise neutralizing bacteria, viruses, as well as other microorganisms or organic matter therein under the control of a computer. In a preferred embodiment, all or a sample of the water to be purified is scanned with an electro-optical scanning device, such as a laser and one or more photoelectric detectors of reflected or fluorescent radiation from organic matter in the water and/or a television camera for imaging particulates in the water. The resulting image and/or radiation signals are computer processed and analyzed to detect the presence of substrates, such as bacteria or toxic chemicals, and to quantify same over a period of time. The information defining codes generated as a result of such computer analysis are directly or indirectly employed to effect automatic control of one or more devices for purifying the water as it flows and/or while it is held in a tank. Such water purifying devices may comprise a computer controlled injector pump operable to effect the flow of a select quantity of one or more chemicals into the water and/or a radiation source such as a generator of microwaves, UV light, laser radiation, or other radiation. Such chemical or radiation is operable to kill or otherwise render harmless organisms or other matter present in the water. As a result of such controlled water purifying action, the operation is optimized with a savings in energy and/or the amount of chemicals used to purify the water. Furthermore, when a chemical agent is employed to kill bacteria, its amount is minimized to reduce the taste of such chemical as well as any other negative effects on persons drinking or bathing in such purified water.

It is a primary object of the invention to employ electro-optical scanning and purifying devices under control of a computer in order to purify water for drinking or bathing.

It is a further object of the invention to detect substrates such as bacteria, viruses, or other organic matter in a fluid.

It is a further object of the invention to quantify substrates such as bacteria, viruses, or other organic matter in a fluid.

It is a further object of the invention to continuously detect and quantify substrates such as bacteria, viruses, or other organic matter in a flowing liquid.

It is a further object of the invention to detect and kill or otherwise neutralize bacteria, viruses, cancerous cell or other organic matter in a body fluid.

Other objects, features, and advantages of the invention will become evident in light of the following detailed description considered in conjunction with the referenced drawings of a preferred exemplary embodiment according to the present invention.

DETAILED DESCRIPTION OF THE INVENTION

Figure 2:
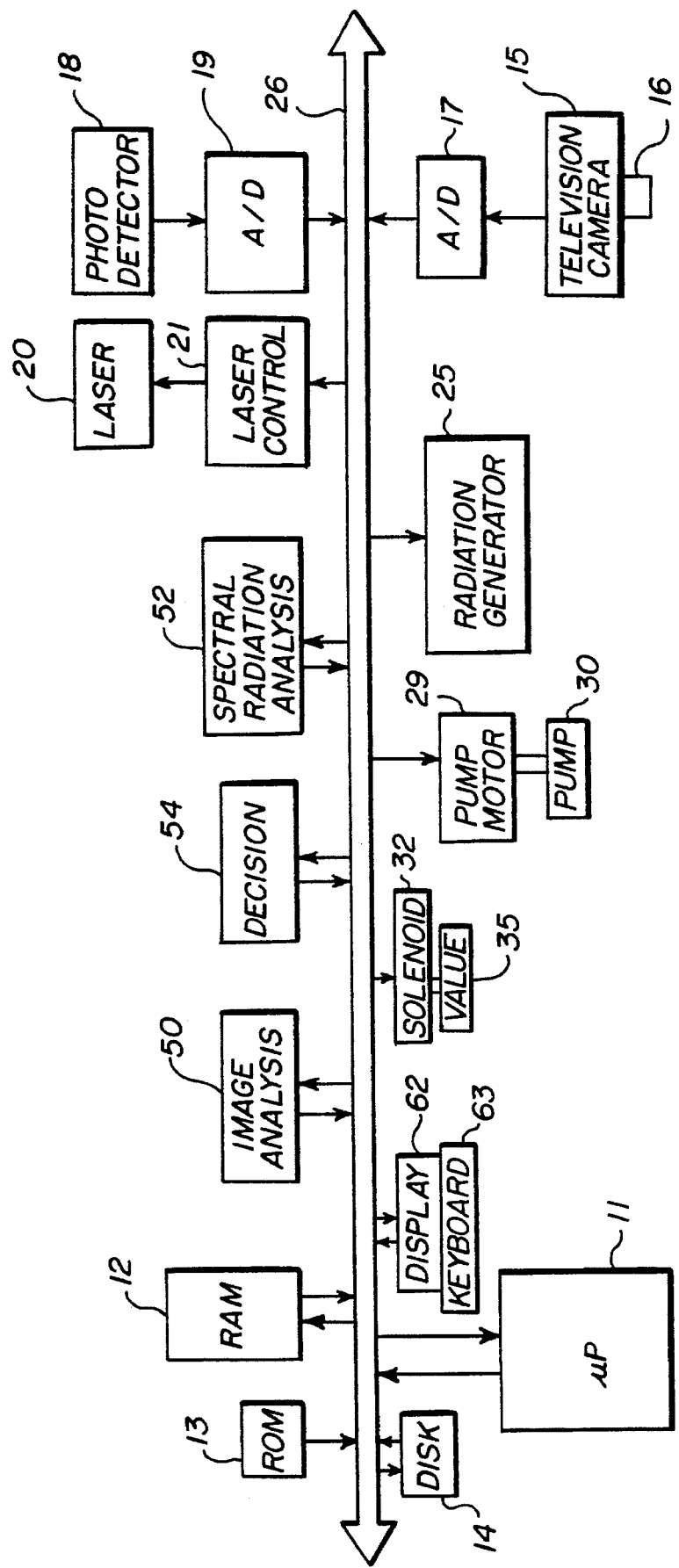
FIG. 2 shows a system for analysis of data generated by electro-optical scanning devices and operation of control elements to purify a fluid.
Figure 3:
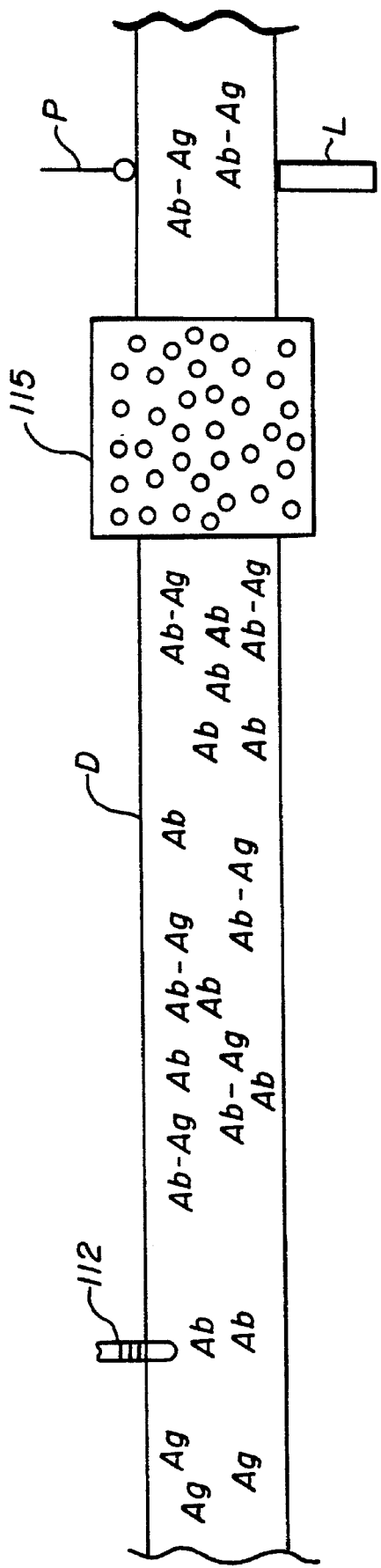
FIG. 3 shows a system for quantizing the amount of substrate in a flowing liquid.

In FIG. 2 is shown a system 10 for detecting disease causing elements in a liquid such as water or body fluid such as blood, quantizing same and automatically computer controlling one or more means or subsystems for killing or deactivating the disease causing or defining elements in the liquid. The system 10 may be utilized to purify drinking or pool water and/or in a modified form, blood in vitro and/or in vive by killing harmful or disease defining bacteria, virus, cancer cells and the like therein.

Figure 1C:
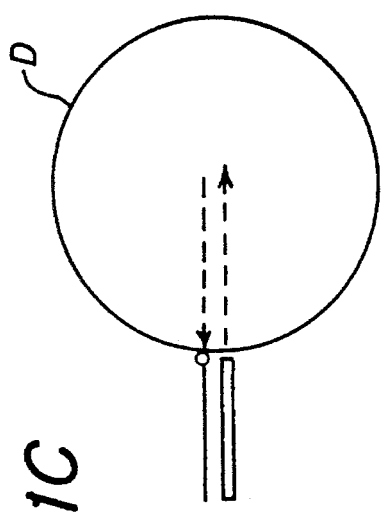
FIGS. 1A through 1B show alternative configurations of a laser and photodetector for detecting microorganisms and other matter within a duct.
Figure 1D:
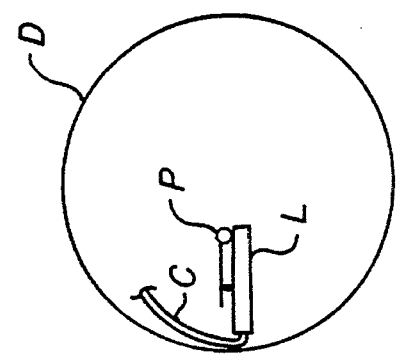
Figure 1A:
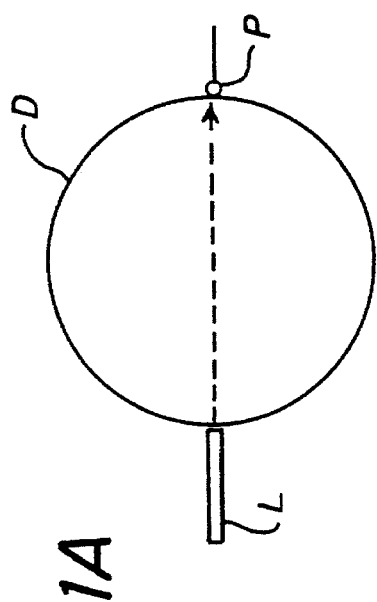
Figure 1B:
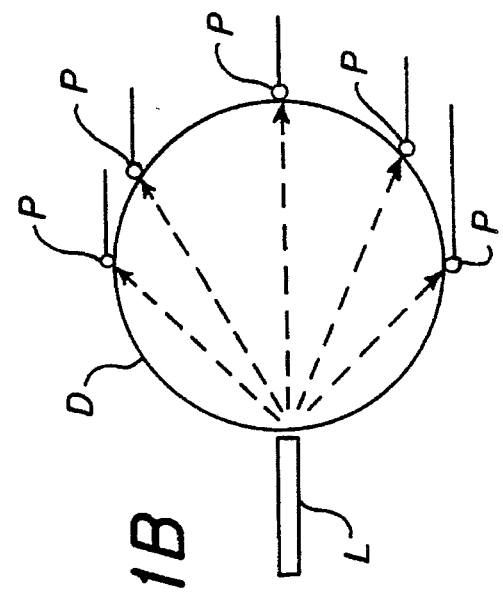

FIGS. 1A through 1D show different alternative arrangements of a laser L and a photodetector P for detecting substrates in a liquid contained within a duct D. The laser L generates a laser beam of fixed frequency or a varying computer controlled group of frequencies or wavelengths which beam (or a plurality of beams from a plurality of lasers L) is passed laterally or oblique to the longitudinal axis of a tube or duct D through which the liquid is flowing. The light beam may also be deflected to scan a plurality of paths in a select (lateral and/or oblique) plane or plurality of planes through the liquid. A transparent window in the duct D, transparent wall of the duct, or the like may pass the laser beam(s) to the liquid and also pass reflections thereof and/or fluorescence or spectral radiation from solids in the liquid back to the photodetector P. The laser and photodetector may be held stationary or may move together in a scanning movement. Alternatively, the laser L and photodetector P may be disposed within the liquid by being mounted in the wall of duct D. The photodetector P may be located relative to the laser L so as to detect scattered or backscattered radiation as shown in FIGS. 1A and 1C, respectively. FIG. 1B shows a plurality of photodetectors arranged so as to detect scattered radiation from laser L or emitted radiation from excited substrates within the duct D or a protruding portion of the wall or an element supported thereby and extending ito the duct passageway. The laser or a light pipe directing such laser radiation L and the photodetector P may also be disposed in the opening of a narrow hypodermic needle or at the end of a catheter C disposed in the tube D, blood vessel, or other body duct as shown in FIG. 1D.

A microprocessor or computer 11 controls the detection and treatment actions by receiving and gating digital detection and control signals to and from various electrically operated devices and subsystems. The microprocessor 11 is shown as connected via a bidirectional data bus 26 to various peripheral components including a RAM 12, a ROM 13, a disk storage device 14, a keyboard 63, a display 62, as well as other components as described below. Scanning of a fluid to detect select elements therein, such as disease indicating or defining bacteria, viruses, fungae, or other types of select substrates is effected by one or more imaging devices and/or spectral radiation detection devices such as photoelectric detector 18 which may be used alone or with a plurality thereof and one or more attendant lasers 20 to scan across a duct such as a pipe through which water or other liquid is flowing or for scanning blood in a blood vessel. The output of detector 18 is a variable electrical signal which is digitized by an analog to digital converter 19 and passed to data bus 26 for analysis by a spectral radiation analysis module 52. The lasers 20 may be tunable so that the wavelengths of their emitted radiation may be program varied under control of computer 11. Such computer control of the laser tuning may be in accordance with a standard protocol or may be varied in accordance with auromatic analysis of previously generated and analyzed scanning signals so as to permit the automatic detection of a variety of different substances or entities in fluid scanned.

In a preferred embodiment, the computed digital code signals output by either or both image analyzing and spectral radiation signal analyzing modules or computers 50 and 52 are applied by microprocessor 11 to a decision module or computer 54 for analysis using expert systems, fuzzy logic and/or neural network techniques, where the aforementioned modules may be either dedicated hardware components or software programs. The output of decision module 54 generates coded command signals for controlling the operation of one or more pump motors 29 operating pumps 30 and/or solenoids 32 operating valves 35 to flow controlled amounts of chemical and/or biological agents to the water or body fluid to kill or otherwise neutralize or affect the detected disease elements therein.

Such computer generated control signals may be applied to control the operation of one or more radiation generators 25 for generating and applying disease organism killing or neutralizing radiation to a select location or locations of the liquid. The duration and intensity of the applied radiation may be computer controlled in accordance with the type(s) and density of the detected disease elements in the liquid.

Also shown in FIG. 2 is a scanning television camera 15 coupled to scan images of an optical or electron microscope 16 scanning either the liquid in the duct or blood vessel D and/or sample(s) of such liquid automatically removed therefrom as a flow, as individual drops, pools thereof or thin films or smears applied by a robot applicator penetrating the flowing liquid. The image signal output of the TV camera 15 is digitized in an A/D converter 17 and passed to bus 26 for analysis by image analyzing module 50. The TV camera 15 may be employed alone or to provide image signals together with spectral or fluorescence signals obtained by one or more photoelectric detectors sensing spectral radiation from disease elements (cancer cells, bacteria, protozoa, viruses, etc.) in the fluid as they are intersected by exciting laser radiation applied as described.

The system described above may be used for purifying water or other fluid by scanning samples of the water and operating purification equipment such as chemical injectors or radiation sources in accordance with the results of the scanning. The system may also be used to scan a body fluid of a patient (eg., blood or lymph) in order to detect organisms such as bacteria, viruses, or cancer cells and neutralizing the organisms so detected with radiation and/or a chemical or biological agent. The scanning device may be disposed within a blood vessel of the patient by means of a catheter or hypodermic needle or samples of the patient's body fluid may be scanned and neutralized extracorporeally. With proper miniaturization of the electronics and mechanical components, the system 10 may be carried by a person or disposed within a body implant housing to continuously scan body fluids for cancer cells or foreign organisms, detect same, and apply laser radiation or inject a drug or other chemical agent to kill or otherwise treat same. The chemical agent may be injected directly from the implant or from a separate injection needle inserted into an artery or vein under control of the onboard computer. Similarly, laser radiation may be transmitted via a light pipe inserted into the body or produced by a laser within the implant.

FIG. 3 shows an embodiment of the present invention where the fluid to be analyzed is passed through a conduit or duct D which may be either a section of a primary pipline transporting the fluid or a sidestream sample from a pipeline or other fluid containing structure. A predetermined quantity of a fluorescent-labeled substance having a specific binding affinity for a selected substrate (such as a bacterium, viral particle, or molecule) whose presence is to be detected or quantified is then injected into the sample stream from injection nozzle 112. The labled binding substance may typically be antibodies Ab, either in the form monclonal antibodies or labeled antiserum containing such antibodies, which react with antigenie determinants Ag on the substrate. After mixing with the sample fluid, the antibodies form Ab-Ag complexes with any substrate present in the fluid. An excess of antibodies is used to ensure that all the substrate present reacts with antibody. Next, the fluid is passed through a reaction vessel 115 in which any unbound antibodies react with immobilized antigen corresponding to antigenic determinants present on the substrate. The reaction vessel 115 may take any number of forms, such as a column of inert material (eg., cellulose or agarose) to which antigen is attached. The amount of immobilized antigen presented to the fluid is such that all unbound antibodies react with the antigen and are thus essentially cleared from the solution. This means that the material within the reaction vessel 115 should be periodically cleaned or changed in order to contain sufficient unreacted immobilized antigen to clear the fluid of unbound antibodies. After passing through reaction vessel 115, the fluid contains labeled Ab-Ag complexes consisting of antibody bound to substrate particles. One type of label which may be conjugated to the antibody is a fluorescent label such as fluorescein or rhodamine which are commonly used in flow cytometry. The Ab-Ag complexes are detected by means of a laser L for exciting the fluorescent dye molecules and a photodetector P for measuring the light scattered and/or emitted by the fluorescent molecules. The laser is operated in a scanning fashion so that the beam intersects with a large portion of the fluid passing by. The signal produced by the photodetector P varies in accordance with the amount of substrate present in the sample fluid and is fed to the computer 11. The computer is thus able to detect whether or not the substrate is present or, by comparing the photodetector signal to standard values and taking into account the fluid flow rate and number of antigenic sites on the substrate particles, identify and quantify the amount of substrate present. The present invention thus allows the continuous monitoring and/or quantification of substrates in a flowing fluid. As described above, if the substrate is detected within the fluid, the computer 11 may then operate a mechanism such as a chemical injector and/or radiation source to destroy or otherwise neutralize the substrate and thus purify the fluid.

The embodiment described above uses labeled antibodies which bind to antigenic determinants on the substrate particles in order to detect their presence. Certain substrates, however, can react with other types of ligands which may be labeled and detected in a similar manner. For example, labeled protein A from *staphylococcus aureus* or lectins such as conconavilin A may be used to detect the presence of immunoglobulins or carbohydrates, respectively, in the sample fluid. Labeled antibodies may also be used in an indirect method in which antibodies directed against the substrate are reacted with substrate particles as described above and then reacted with labeled anti-Ig antibody to allow the detection identification and/or quantification of the substrate.

Although the invention has been described in conjunction with the foregoing specific embodiments, many alternatives, variations, and modifications will be apparent to those of ordinary skill in the art. Those alternatives, variations, and modifications are intended to fall within the scope of the following appended claims.

What is claimed is:

1. A method for purifying water comprising the steps of:

scanning a select amount of water with a laser, irradiating substrates in the water with laser radiation and generating scanning signals containing information indicative of the presence of select substrates in the water with a photodetector for detecting radiation emanating from said substrates;

wherein said laser radiation is controllably varied during scanning to detect different biological substrates in the water;

computer processing and analyzing said scanning signals and code signals relating thereto; and employing said code signals to control the operation of a device for neutralizing the substrates so detected.

2. A method in accordance with claim 1 wherein said scanning step is further performed with a television camera for imaging substrates in the water.

3. A method in accordance with claim 1 wherein said scanning step is further performed with a television camera for imaging substrates in the water and further wherein said camera scans magnified images.

4. A method in accordance with claim 1 wherein said scanning step is further performed with a television camera for imaging substrates in the water and further wherein the laser illuminates the water scanned by the camera.

5. A method in accordance with claim 1 wherein said scanning step is performed with a television camera for imaging substrates in the water and further wherein the laser scans a field scanned by the camera.

6. A method in accordance with claim 1 wherein said neutralizing step is performed by injecting a chemical agent into the water.

7. A method in accordance with claim 1 wherein said select substrates are microorganisms and said neutralizing step is performed by irradiating the water with lethal radiation.

8. A method in accordance with claim 1 wherein said select substrates are microorganisms and said neutralizing step is performed by irradiating the water with microwave radiation.

9. A method in accordance with claim 1 further comprising the steps of using said scanning signals to quantify the amount of substrates in the water, generating a code signal indicative thereof, and performing said neutralizing step in accordance with said quantity indicating code signal.

10. A method in accordance with claim 1 wherein said radiation detected by said photodetector is laser radiation scattered by said substrates.

11. A method in accordance with claim 1 wherein said radiation detected by said photodetector is fluorescence radiation emitted from substrates electronically excited by said laser radiation.

12. A method in accordance with claim 1 wherein said laser radiation is controllably varied during scanning to also detect different chemical substrates in the water.

13. A method in accordance with claim 1 wherein said laser radiation is controllably varied in accordance with previously generated scanning signals.

14. A method in accordance with claim 1 further comprising the step of generating code signals corresponding to different deleted substrates.

15. A method for purifying water comprising the steps of:

scanning a select amount of water with a television camera to generate image signals relating thereto:

scanning the select amount of water with a laser;

computer processing and analyzing said image signals and generating code signals relating thereto containing information indicative of the presence of select substrates in the water;

employing said code signals to control the operation of a device for neutralizing the substrates so detected.

16. A method in accordance with claim 15 wherein said camera scans magnified images.

17. A method in accordance with claim 15 wherein said laser illuminates the water scanned by the camera.

18. A method in accordance with claim 15 wherein a laser is the device for neutralizing the substrates so detected.

* * * * *